(12) United States Patent
Bourget Fussy (10) Patent No.: US 11,464,350 B1
(45) Date of Patent: Oct. 11, 2022

(54) WEIGHTED LAP PAD

(71) Applicant: Renee Bourget Fussy, Shakopee, MN (US)

(72) Inventor: Renee Bourget Fussy, Shakopee, MN (US)

(*) Notice: Subject to any disclaimer, the term of this patent is extended or adjusted under 35 U.S.C. 154(b) by 586 days.

(21) Appl. No.: 16/196,021

(22) Filed: Nov. 20, 2018

Related U.S. Application Data (60) Provisional application No. 62/590,065, filed on Nov. 22, 2017.

(51) Int. Cl.
| | | |
|---|---|---|
| *A47G 9/02* | (2006.01) | |
| *A47G 9/00* | (2006.01) | |
| *A61M 21/02* | (2006.01) | |
| *B43L 1/00* | (2006.01) | |
| *A63F 11/00* | (2006.01) | |

(52) U.S. Cl.
CPC .......... *A47G 9/0215* (2013.01); *A47G 9/007* (2013.01); *A63F 11/00* (2013.01); *B43L 1/00* (2013.01); *A47G 2009/005* (2013.01); *A61M 21/02* (2013.01)

(58) Field of Classification Search
CPC . A61M 21/00–02; A47G 9/0207–0233; A47G 9/08–109
See application file for complete search history.

(56) References Cited

U.S. PATENT DOCUMENTS

| | | | | |
|---|---|---|---|---|
| 5,584,086 A * | 12/1996 | VanWinkle | .......... | A47C 20/021 5/636 |
| 6,383,130 B1 * | 5/2002 | Wade | .................... | A61M 21/00 600/27 |
| 6,463,608 B1 * | 10/2002 | Moe | ...................... | A01M 31/00 5/646 |
| 7,513,001 B1 * | 4/2009 | Leach | .................. | A47G 9/1045 5/655 |
| 8,205,283 B1 * | 6/2012 | Russell | .................. | A47C 7/383 5/636 |
| 8,695,137 B1 * | 4/2014 | Hanson | .................... | A47D 5/00 5/655 |

(Continued)

OTHER PUBLICATIONS

Padjit Weighted Activity Lap Pad, https://www.southpaw.com/sensory-integration/si-new-products/padjittm-lap-pad.html, back-dated at least to Apr. 12, 2015, retrieved Feb. 12, 2021. (Year: 2015).*

(Continued)

*Primary Examiner* — Thaddeus B Cox
(74) *Attorney, Agent, or Firm* — Anthony J. Bourget (57) ABSTRACT

A weighted lap pad comprising a base having a body-conforming configuration adapted to be placed across a lap of a seated user, the base having a plurality of channels having weights permanently enclosed within respective channels, the weights having a cumulative weight of greater than 2 pounds and a transparent window positioned at a surface of the base and in part defining a device pocket configured to receive a paper device or electronic touch screen device. The transparent window and associated pocket allowing a user to experience visual and multi-media sensation while simultaneously receiving tactile sensation of the weighted pad. The electronic device also allows for a variety of user control and sensory feedback options.

19 Claims, 7 Drawing Sheets

(56) References Cited

U.S. PATENT DOCUMENTS

| | | | | |
|---|---|---|---|---|
| 8,707,485 | B1* | 4/2014 | Conley | A47G 9/109 5/636 |
| 8,931,127 | B1* | 1/2015 | Moses | A47G 9/10 5/652 |
| 2009/0149698 | A1* | 6/2009 | Tastard | A61M 21/00 600/27 |
| 2010/0175161 | A1* | 7/2010 | Jarboe | A45C 3/14 2/69 |
| 2013/0205471 | A1* | 8/2013 | Alvarez | A41D 13/0512 2/202 |
| 2014/0231277 | A1* | 8/2014 | Ponski | A45C 11/00 206/38 |
| 2015/0297003 | A1* | 10/2015 | Ahroon | G06T 7/33 206/38 |
| 2016/0029821 | A1* | 2/2016 | Atkinson | A47G 9/10 5/636 |
| 2016/0345760 | A1* | 12/2016 | Pesale | A47G 9/109 |
| 2017/0127854 | A1* | 5/2017 | Bui | B60N 2/28 |
| 2017/0164663 | A1* | 6/2017 | Korenek | B60N 2/80 |
| 2017/0208881 | A1* | 7/2017 | Leathers | A41D 23/00 |
| 2018/0000171 | A1* | 1/2018 | Pacheco | A41D 31/02 |
| 2018/0043809 | A1* | 2/2018 | Probst | B60N 3/002 |
| 2018/0146807 | A1* | 5/2018 | Silver | A47G 9/1045 |
| 2019/0060604 | A1* | 2/2019 | Smith | A61M 21/02 |

OTHER PUBLICATIONS

Busy Fingers Fidget Lap Pad, https://funandfunction.com/busy-fingers-tm-fidget-lap-pad.html, backdated at least to Apr. 23, 2015, retrieved Feb. 12, 2021. (Year: 2015).*

* cited by examiner

WEIGHTED LAP PAD

BACKGROUND OF THE INVENTION

1. Field of the Invention

This invention relates to the field of weighted devices or apparel for addressing sensory needs of people, and particularly to weighted lap pads which provide extra sensory stimulation to a user.

2. Background Information

Weighted lap pads are used as comfort devices to provide extra sensory stimulation to users. The user will place the pad on his or her lap and may often naturally relax due to the calming impact of the weighted pad. Some weighted lap pads included fidgets to allow for additional sensory input and/or entertainment.

Applicant is aware of one lap pad device having sensory attachments, such as that shown in U.S. patent application Ser. No. 12/316,093 (Publication No. US 2009/0149698). Other lap pads are available which include segmented channels bearing weight material, and still other lap pads include pockets configured for insertion of a person's hands. Such pockets also include a fidget hidden within the pocket.

While the foregoing may have beneficial features, there is room for improvement.

SUMMARY OF THE INVENTION

In one aspect the invention pertains to a device that provides tactile stimulation combined with multimedia stimulation via an electronic display device.

In a further aspect the invention comprises a weighted lap pad having a pocket and associated transparent window configured such that an electronic or other device positioned in the pocket is visible to a user of the lap pad. The lap pad is filled or partially filled with flowable material to provide weight stimulation to a user of the pad and to conform to the legs or lap area or other part of the user's body. The pocket receives a device, such as an electronic display device or a game paper such as word seek or other activity, where the device is protected while still being available for activity. In further aspects the lap pad includes a hand pocket into which a user may insert their hand, and a fidget is also provided within the hand pocket. In some aspects two hand pockets are provided and allow a user to touch their hands.

In a further aspect the invention includes a weighted pad with a pocket configured to receive an electronic display device viewable through the pocket, with the electronic device programmed to activate various sensory stimulation mechanisms associated with the pad, and such that a user of the pad and associated device can operate the additional stimuli producing mechanisms, such as speakers, temperature control, vibrators, bone conductors, or other stimulation mechanisms. Data is also recorded to monitor the progress of cognitive ability or changes when utilizing a device positioned within the transparent pocket.

The above partial summary of the present invention is not intended to describe each illustrated embodiment, aspect, or every implementation of the present invention. The figures and detailed description and claims that follow more particularly exemplify these and other embodiments and further aspects of the invention.

While the invention is amenable to various modifications and alternative forms, specifics thereof have been shown by way of example in the drawings and will be described in detail. It should be understood, however, that the intention is not necessarily to limit the invention to the particular embodiments, aspects and features described. On the contrary, the intention is to cover all modifications, equivalents, and alternatives falling within the spirit and scope of the invention and as defined by the appended claims.

DETAILED DESCRIPTION OF THE INVENTION

Figure 1:
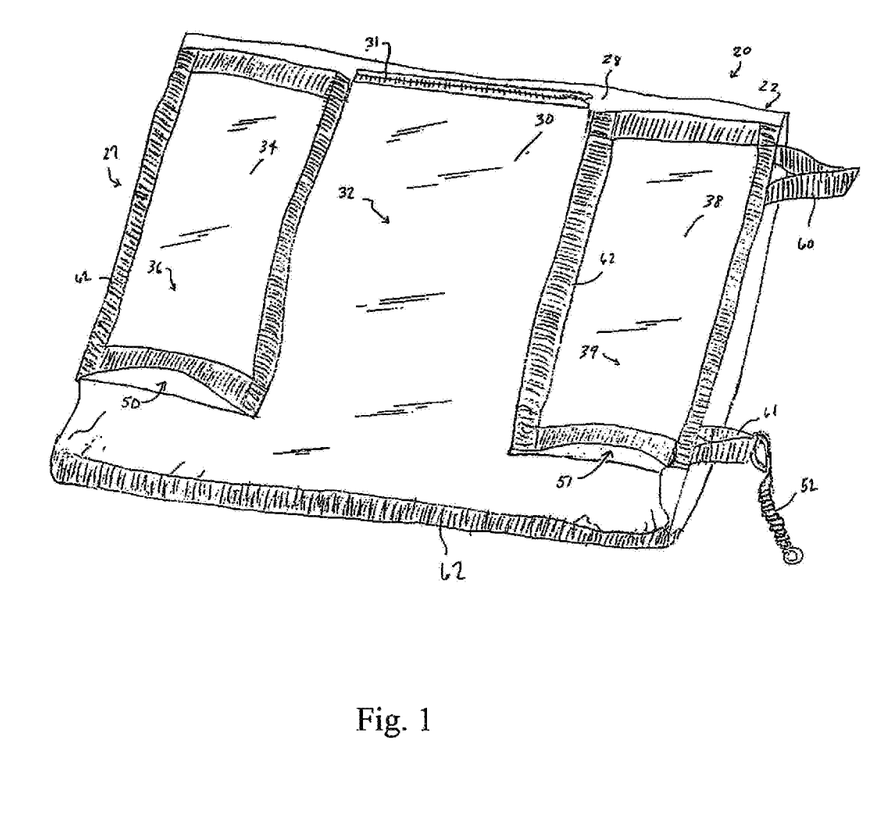
FIG. 1 is a perspective view of a device made in accordance with one aspect of the present invention.

Referring to FIGS. 1-7, aspects of a weighted device for conforming to a person's body to provide tactile stimulation are shown. FIG. 1 depicts device 20 which in one aspect is a weighted lap pad 20 having a base 22 configured to conform to a person's body, including configured to be placed across a lap of a seated user. The lap pad 20 is especially comforting and useful for persons requiring or desiring tactile stimulation. As described below, lap pad 20 is also visually stimulating and provides for a variety of activity events due to the presence of a transparent window 30 and associated device pocket 32.

Figure 3:
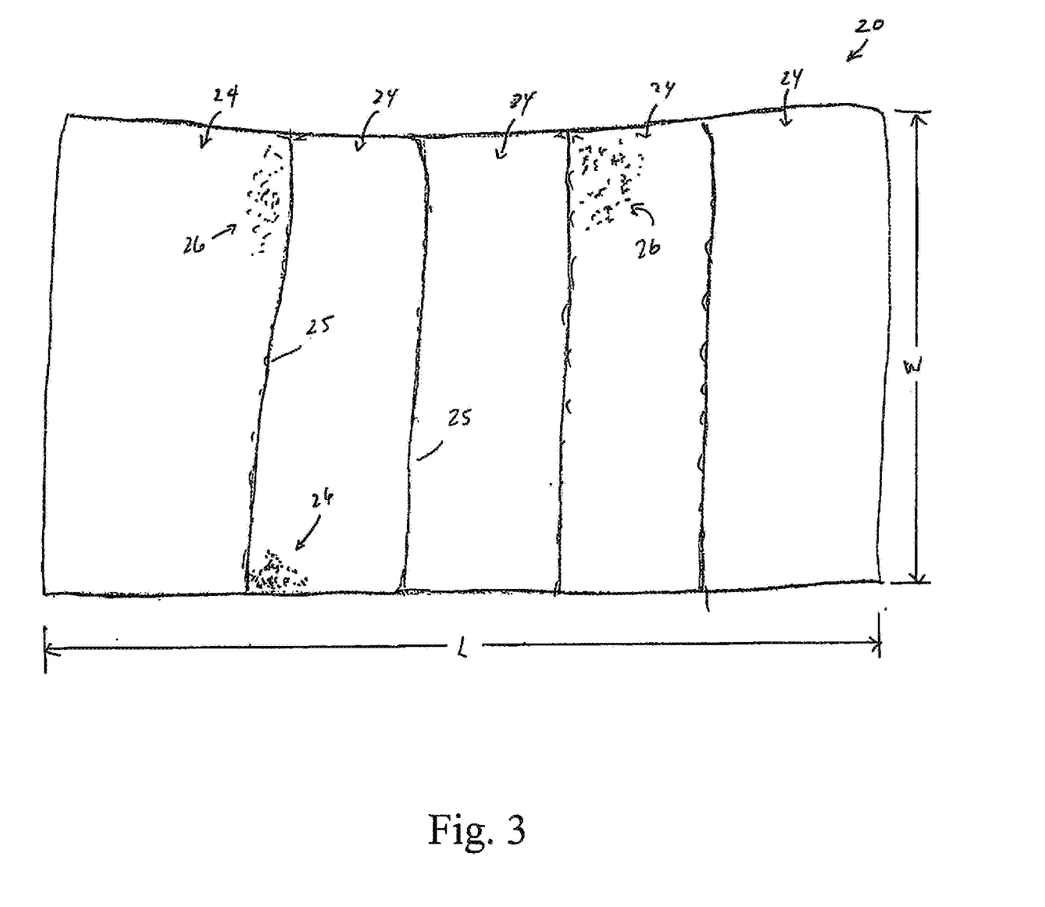
FIG. 3 is a section view depicting an inside portion of the device of FIG. 1.

In one aspect base 22 includes a plurality of channels 24 in which weight material 26 is enclosed (See FIG. 3). In one aspect the channels 24 span the entirety or substantially the entirety of the length and width of device 20. In other aspects the channels 24 are configured to span less than the entirety of the length and/or width of the device. Channels 24 may also be configured as different shaped segments to enclose the weighted material 26. In one aspect device 20 includes five separate channels 24. Additional, or fewer, channels 24 may be utilized as desired. Use of five channels allows for a comfortable distribution of the weighted material 26 within base 22. Having the channels or segments prevents the weighted material 26 from collecting at one portion within the base (as would happen if only a single segment or cavity were used for the interior spanning the base 22). In one aspect weighted material 26 includes poly pellets which allow base 22 to conform to the shape of a person's body. The pellets are flowable and adjust or settle to conform within a channel and cause the lap pad 20 to settle upon and conform to the physiology of a user. In other aspects, material 26 may comprise steel shot, pea gravel, sand, or other flowable weighting material, or a combination of the same.

Figure 2:
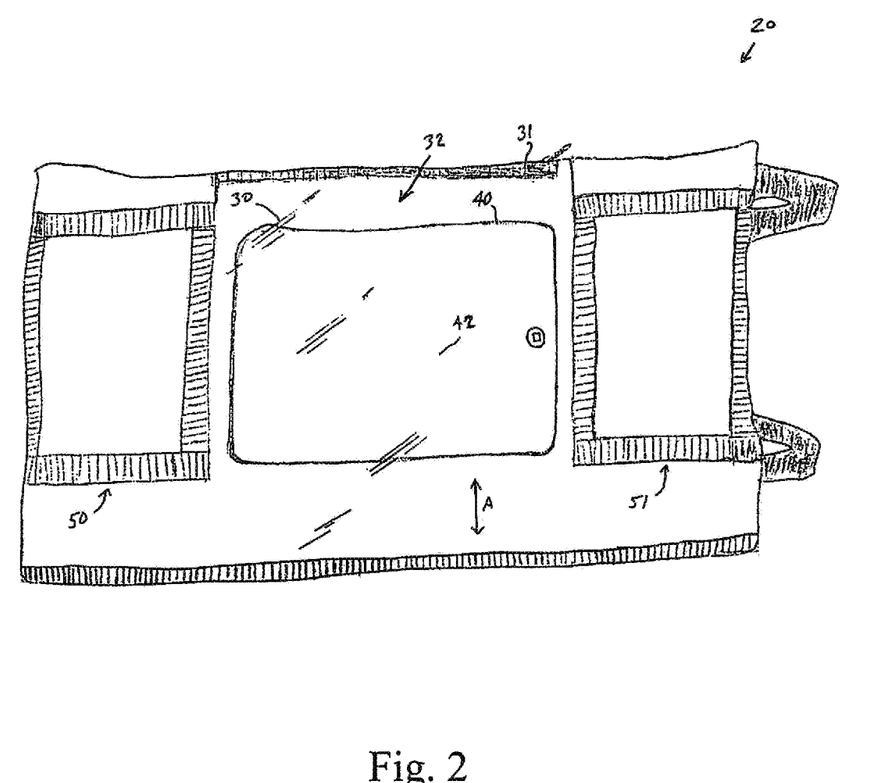
FIG. 2 is a top view of a modified device shown in FIG. 1 and depicting a tablet device inserted therein.

FIG. 1 and FIG. 2 show lap pad 20 having a transparent window 30 positioned at an outer or top surface 28 of base 22. Window 30 in part defines a device pocket 32. An activity device 40 is inserted into pocket 32. Activity device 40 provides visual and/or auditory and/or physical stimulation and active opportunities for a user (in addition to the traditional physical stimulation provided by the weighted and body conforming base 22). Window 30 is transparent. In one aspect window 30 is made of vinyl or other transparent plastic. Window 30 is secured to base 22 in one instance by stitching a sheet of vinyl plastic along three edges of a perimeter of the plastic sheet, leaving a top edge free and thus creating, in part with a top surface 28 of base 22, pocket 32. A fastener 31 is used to enclose the opening of pocket 32 to secure a device 40 within the pocket. In one aspect the fastener 31 is a zipper. In other aspects a fastener 31 may include a hook and loop type fastener or other fastening device.

Activity device 40 in one aspect is a tablet device, notebook computer, or electronic device having a display. In one aspect the device 40 has a touch screen display 42 that operates by a person touching the screen. Window 30 is configured such that a person touching window 30 is able to operate the touchscreen 42 of device 40. In this manner, a user may enjoy use of device 40 in the normal course. In one aspect window 30 is a continuous sheet of plastic. In other aspects a perforation or perforations may be included in window 30 to accommodate audio feedback or other direct exposure or access to the device 40. Activity device 40 in other aspects include non-electronic devices, such as crossword puzzles, word searches, seek-and-find material, bingo cards, lists, trivia cards, school itinerary/schedule or other devices. Activity device 40 may also include photographs or pictures. A user may include pictures of family and friends or pets or other activity device (for visual and cognitive stimulation). Window 30 is waterproof and easily wipes clean from spills or messes. Window 30 is also configured to receive dry-erase or other markings so that a user may perform marking activities on window 30 corresponding to an underlying activity device 40 (i.e. crossword puzzle or word search) positioned within pocket 32.

Pocket 32 is configured such that it may receive a device 40 such as an Apple iPad or other tablet device. The pocket 32 and window 30 shown in FIG. 1 are generally configured to receive a device 40 in a portrait orientation. The pocket 32 and window 30 shown in FIG. 2 are generally configured to receive a device 40 in a landscape orientation. As shown in FIG. 2, device 40 fits into pocket 30 in a landscape orientation. Device 40 may also be positioned vertically. Device 40 may slide upward or downward in the direction of arrow A. In one aspect pocket 32 is configured to allow for slight movement of an iPad device in the direction perpendicular to direction A. In alternatives, the pocket 32 may be accessed at a side location. In one aspect pocket 32 is configured to receive more than one device 40. A combination of different devices 40 may be used within pocket 32, such as a tablet computer and a word search device, or two electronic devices having touch screens, or electronic devices without touch screens.

In operation, lap pad 20 having window 30 is configured to allow for monitoring cognitive ability of a user. For instance, a device 40 such as a word search may be used repeatedly to track the progress (or deterioration) of a user's cognitive ability. The same word search device 40 may be used at different times to chart the progress of use. The user may mark the window 30 by using a dry-erase marker and an assistant or health worker may record the markings to compare against past or future markings where the identical device 40 is inserted into pocket 32. In other aspects a worker will take a photograph or otherwise preserve the results. The device 20 accommodates efficient use by people who may spill materials such that staff may efficiently wipe clean the window 30 and remaining components of device 20.

In further reference to FIG. 1 and FIG. 2, additional transparent window or windows and corresponding pockets are provided on base 22. An additional device 40 or devices 40 may be inserted into respective pockets 36, 39. In further aspects, base 22 is also equipped with a hand pocket 50 or pockets 50 into which a user may insert their hand. A hand pocket 50 may be lined with a "minky" or soft material (or other tactile sensory material). A "minky" material provides a comforting sensation for a user. In one aspect a pair of hand pockets 50, 51 are provided so that a user may place both hands within base 22.

Figure 4:
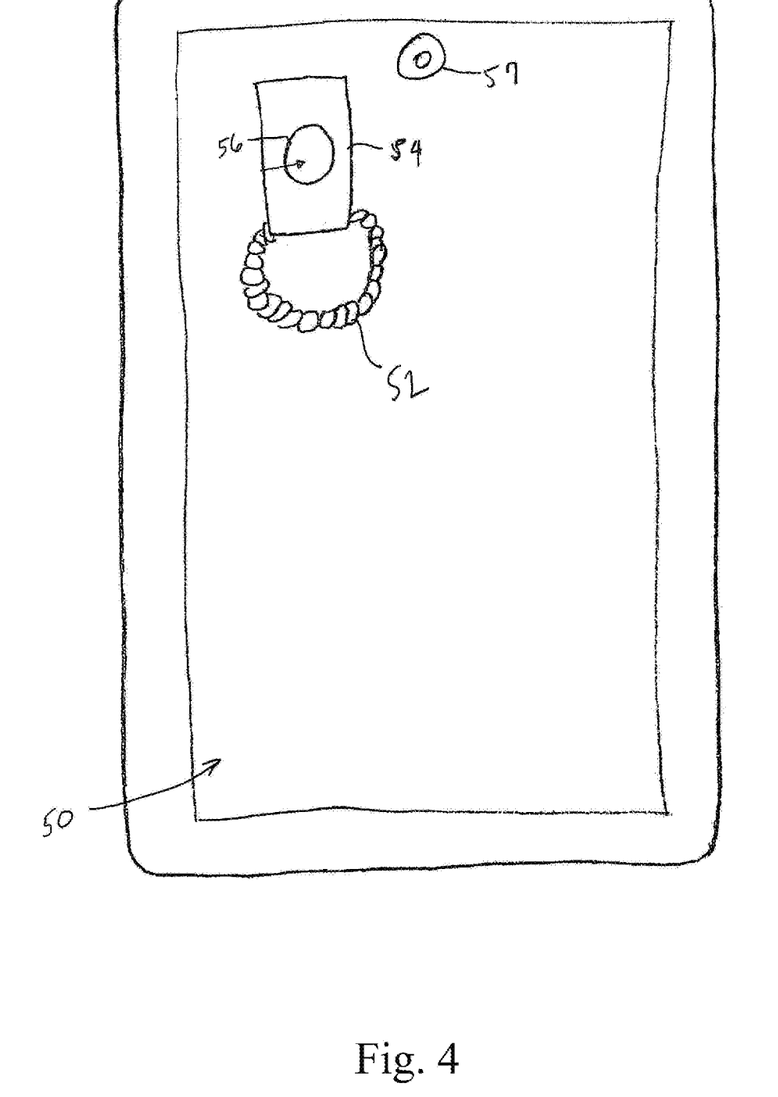
FIG. 4 is a top view depicting an inside portion of a hand pocket feature of the device of FIG. 1.

In further aspects and with respect to FIG. 4, a fidget 52 or plurality of fidgets are positioned within hand pocket 50, 51. In one aspect fidget 52 is selectively removable and/or connected to a removable ribbon 54. A fidget 52 may include any number of a variety of fidgets commonly available, including fidgets of a stretching variety that may expand. Fidget 52 is hidden within pocket 50, 51. A ribbon 54 in one aspect includes a heavy duty snap 56 or other fastener to fasten to an internal receiving snap 57 or other fastener to secure fidget 52. Multiple fidgets 52 may be included and interchanged from within hand pockets 50, 51. In further aspects, pocket 50 may extend within base 22 in many different varieties. For instance, pocket 50 may be configured to allow a person's hand to insert within pocket 50 and be positioned beneath window 30. In other aspects pocket 50 is configured to allow communication into pocket 51 (or a pathway is stitched within base 22 to allow access or limited access between pockets 50, 51. A single seam line or narrow dividing region may separate pockets 50, 51 to allow a user to sense the presence of his or her hands on either side of the seam without actually touching hands. Having openings to respective pockets 50, 51 separated across opposite sides of pocket 32 allows for ease of entry of a person's hands into pockets 50, 51 without undue twist or extension of the wrists. As shown in FIG. 1, pockets 50, 51 generally align with the top of a user's thighs when lap pad 20 is positioned on a seated user's lap. In other aspects the openings to pockets 50, 51 may be slightly angled to encourage efficient ergonometric insertion of a user's hands into the pockets 50, 51. Hand pocket 50 may be included with or without an associated device pocket 36 positioned atop hand pocket 36. The device shown in FIG. 1 includes three device pockets 32, 36, 39, each with a respective transparent outer window 30, 34, 38.

Figure 6:
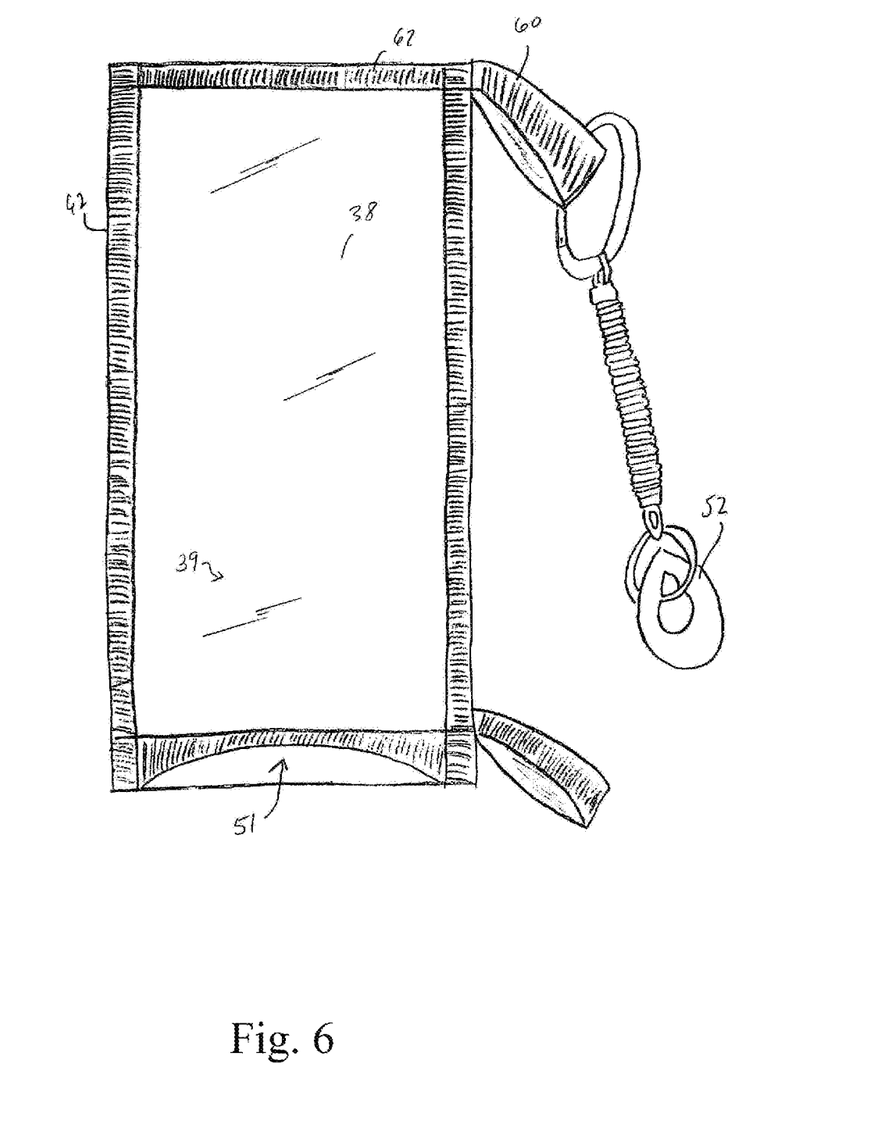
FIG. 6 is a partial top view of a component of the device shown in FIG. 1.

FIG. 6 is a partial top view of a component of the device shown in FIG. 1, with a portion of a lap pad 20 having a transparent window 34 positioned above hand pocket 51. Transparent window 34 also defines in part device pocket 39. Pocket 39 is configured to receive a device 40, which may be inserted through a top opening of pocket 39. The top opening may be an opening provided at ribbon 62, and a closure mechanism such as a zipper or hook-and-loop fastener may be used to secure a device 40 within the pocket 39. Pictures of family or friends may be inserted as device 40, or other devices 40 as referenced herein may be included. The transparent window 34 and associated pocket 36 may also be a storage unit for fidget devices.

In a further aspect the invention includes a firm substrate (such as card stock or thin hardened plastic sheet) positioned within pocket 32 or behind layer 28 beneath pocket 32 in order to provide tension or to urge an inserted device 40 (such as an iPad) against window 30. Such tightening assists in providing a tight fit of window 30 against the touch screen 42 of device 40 for acceptable touch screen operation. In one aspect the firm substrate is removable. In further aspect window 30 is tensioned into position with hook-and-loop fasteners which may also be lifted and adjusted to vary the tension of window 30 upon device 40. Achieving a tight or flat orientation of window 30 against touch screen 44 is desired for when using device 40 where fast and accurate response to touch screen movement is desired.

Device 20 includes hang straps 60, 61 which in one aspect include a nylon strap looped and stitched within base 22. The straps 60, 61 are separated and configured to allow device 20 to hang on a wall. A series of lap pads 20 may be aligned along a wall for storage and for quick release/use. The channels 24 allow devices 20 to align relatively flat against a wall (instead of having all weight material 26 flow to a bottom of the device 20 when hung. Devices 40 may be inserted into pockets 32, 36, 39 while device 20 is hung via straps 60, 61. Straps 60, 61 in some aspects are used for attachment of a fidget or fidgets, including chew toys or devices. The use of these straps allow for greater mobility of the device.

In one aspect lap pad 20 has a length of approximately 24 inches and a width of approximately 14 inches. Window 30 and pocket 32 are configured to hold a device 40 including electronic devices and/or sheets of paper or other materials having a dimension of approximately 8½ by 11 inches or up to 14 inches. The thickness of lap pad 20 may vary and in one aspect is approximately 2 inches thick. In one aspect lap pad 20 has five internal segments or channels 24 containing pea gravel and weighting about 15 pounds. In other examples the collective weight of the flowable weight material 26 ranges from 2 pounds up to 15 pounds, although higher weights are also contemplated provided they are not unduly uncomfortable or harmful to a person having the device 20 positioned on a lap. In one aspect the base 22 is made of Cordura nylon or denim, with Grosgrain ribbons 62 providing border connection and support and a durable quality. The materials resist tears and punctures. Multiple layers may be used for construction, with seams sewn through layers as needed and to create the channels 24. In that regard and with reference to FIG. 3, an inner view of base 22 is shown with multiple channels 24 depicted. FIG. 3 depicts an internal section/area of base 22. Stitch lines 25 depict separation lines or stitchings between respective channels 24. In one aspect the respective channels 24 are stitched along the perimeters of the channels to permanently seal the weight-material 26 therein. The perimeters may be sealed using other techniques. A representative sample of weight-material 26 is shown. It may be appreciated that the material 26 may fill (or substantially fill) each of the channels which are fully enclosed. Weight material 26 in one aspect is permanently enclosed within segments or the channels 24. In one aspect the weight material 26 is flowable. In aspects the weight material is sealed within respective channels 24 or compartments. A user who is wheel chair bound will benefit from the weight of device 20. Device 20 somewhat limits a user's ability to rise up from a seated position without assistance and decreases likelihood of injury due to falls. Use of a device 40 within window 30 in some aspects provides comfort and stimulation to a user and in some instances lessens the likelihood of a user seeking to rise up from a seated position.

Figure 5:
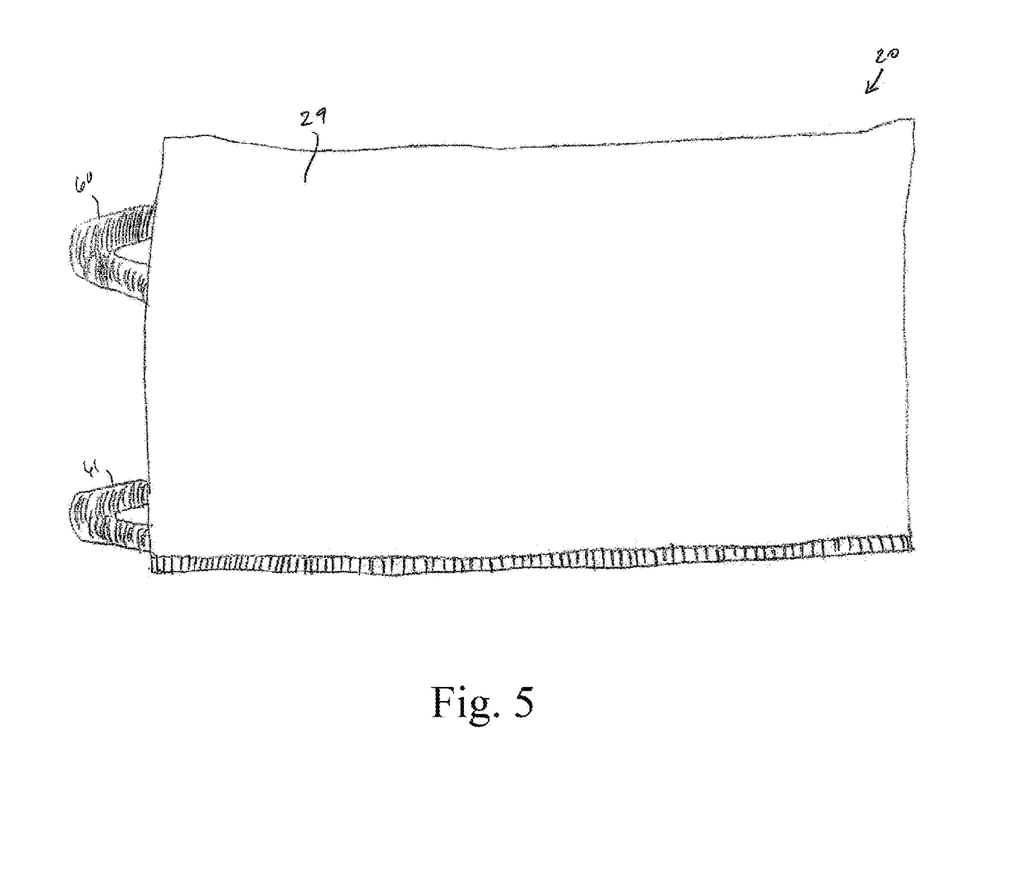
FIG. 5 is a bottom view of the device of FIG. 1.

In a further aspect the invention comprises a weighted hand muff where pockets 50, 51 are separated by a space (the space may or may not include a window 30 or pocket 32) such that pockets 50, 51 are connected within base 22. Such configuration allows for comforting hand-to-hand tactile sensation together with the weight and body confirming tactile sensation of a weighted lap pad. FIG. 5 depicts one aspect of a bottom surface of the device of FIG. 1.

In a further aspect lap pad 20 is configured as a lap pad and backpack combination, and in yet further aspects lap pad 20 is configured as a covert (i.e., disguised) backpack (i.e., device 20 has the appearance of a back pack having shoulder straps and pocket(s), yet is in fact a lap pad 20. In one aspect, straps 60, 61 are configured to extend along the bottom surface 29 and connect to an opposite side of base 22 to form backpack-like straps for carrying device 20. A design (not shown) is provided at bottom surface 29 to replicate an image of a backpack.

Use of window 30 and a device 40 positioned within pocket 32 also provides an opportunity for self-interaction, especially where device 40 includes a camera. A user may see her own image in device 40 and modify the same to create artwork or otherwise entertain herself and others. The device 40 as a tablet will also allow for playing of video or movies or other education or entertainment activities.

In further aspects, device 20 is equipped with a bone conduction mechanism to impart vestibular and somatosensory stimulation through bone conduction of sound waves to skeletal bones. In one aspect, the tablet, smartphone or other device 40 having visual stimuli via a screen is also configured to impart a signal or activate the bone conduction mechanism. In this way, a user playing a game or operation of other activity on device 40 will receive additional sensory stimulation. The sensory information in one aspect is synchronized with images that are displayed on the device 40. Device 40 in one aspect includes interactive software which displays images on a screen of the device while also integrating with electronics of device 20 to coordinate the display of images (or use of sounds or other stimuli) with coordinated vibration (or other stimulus) of device 20. Other stimulation mechanism are used in other aspects of the invention and in conjunction with the device 40 visible through window 30, including vibrating devices, sound mechanism, heat/cooling elements, odor releasing mechanisms, or other sensation producing mechanisms. The foregoing in one aspect are coordinated with the display device 40 so that a user can either control or sense the interactions on the screen with the sensory producing devices. For instance, pressing a button on screen 42 (through window 30) in one aspect will trigger a bone conduction mechanism (or one of several other sensory mechanisms). In one aspect, a software program or app is provided at device 40 to allow a user to operate the software program on the device 40 which in turn triggers one or more of the foregoing sensation producing mechanisms. In one aspect data is collected by device 40 or from lap pad 20 and used for historical comparison and reporting of user based activities. In one aspect data is wirelessly transmitted to other computing devices or servers to assemble the information for reports, diagnosis, therapy and other uses. A system having a plurality of lap pads 20 may also be networked and data collected and aggregated for comparison, reporting, diagnosis and study of big data structures.

A further aspect of the invention includes a lap pad 20 according to the present disclosure combined with an electronic computing device positioned within pocket 32. Such combination provides a unique user experience whereby interaction with the device 40 is configured to operate additional sensory stimuli, such as generation of audible sound, bone conduction sound, vibration, heat/cold temperature adjustment, fragrance release, vibration. The combination lap pad 20 and device 40 also allows for collection and use of data pertaining to the sensations experienced and/or introduced by a user and to compare the same to historical data.

Figure 7:
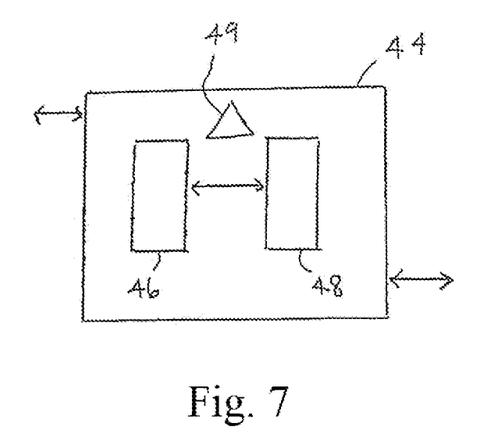
FIG. 7 is a front view of one aspect of a component for use in conjunction with the present invention.
Figure 8:
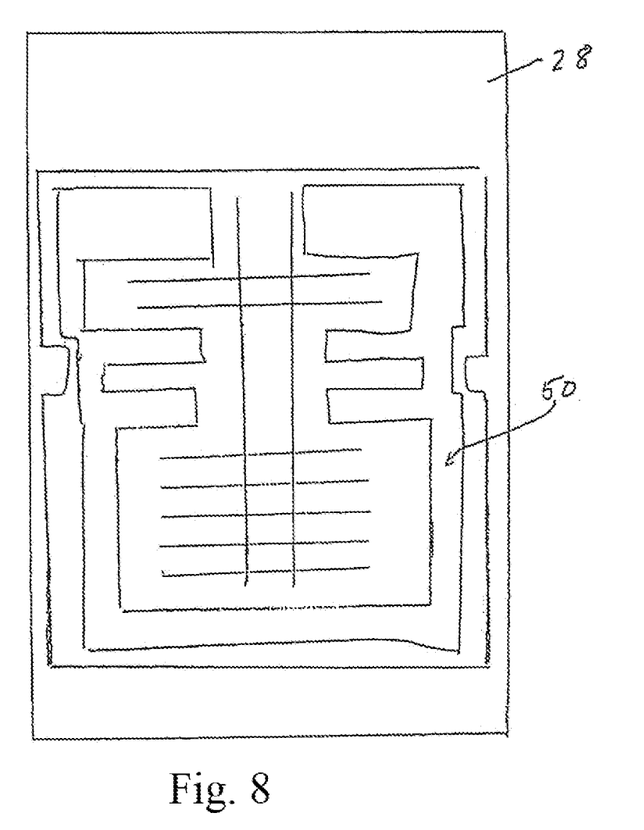

With reference to FIG. 7, in one aspect lap pad 20 also includes a controller 44 which includes a processor 46 and a memory 48 and a computer program stored in memory. Controller 44 receives information from various devices such as sensors, antenna and device 40 and compares the information to one or more thresholds or data stored in memory 48. Based on the comparison, controller 44 may activate other systems or control other steps. Controller 44 may also adjust systems based on user input setting target thresholds or data or overriding aspects of controlled systems or objects. Controller 44 may be informed of target thresholds or comparison data by receiving user input via a user interface device and storing the input in memory 48. Radio signal data or other data or thresholds may be stored in memory 48 by sending signals and information wirelessly to controller 44 and/or to device 40. A wifi unit 49 may receive wireless control data and pass it to controller 44. Wifi unit 49 may be associated directly with controller 44 or may comprise a separate component. Wifi unit 49 may also comprise a Blue Tooth component for use in sending and receiving wireless signals. For instance, unit 49 and/or controller 44 or other chip or board may be configured to send and receive blue tooth wireless data for operation and information distribution. The blue tooth wireless capabilities of a device 40 may be paired with the blue tooth capabilities of device 20. In this manner an efficient data communication may be established for the control operations and sensory stimulus of a user. A computer program (software) in one aspect allows for use and control of the various sensation mechanism presented herein. An application software program stored or used on device 40 may also be used to control the operations of device 20.

In one aspect an electronic device is incorporated within lap pad 20, and such electronic device may be configured with a processor, memory and computer program for operation of the sensation mechanisms and/or operation with an inserted device 40. The term processor is not limited to those integrated circuits referred to in the art as a processor, but broadly refers to a computer, an application specific integrated circuit, and any other programmable circuit. The processors execute instructions, or computer programs, stored in the memories of the device 20. The memory or memories can be implemented using any appropriate combination of alterable, volatile or non-volatile memory or non-alterable, or fixed, memory. The alterable memory, whether volatile or non-volatile, can be implemented using any one or more of static or dynamic RAM (Random Access Memory), a floppy disc and disc drive, a writeable or re-writeable optical disc and disc drive, a hard drive, flash memory or the like. Similarly, the non-alterable or fixed memory can be implemented using any one or more of ROM (Read-Only Memory), PROM (Programmable Read-Only Memory), EPROM (Erasable Programmable Read-Only Memory), EEPROM (Electrically Erasable Programmable Read-Only Memory), an optical ROM disc, such as a CD-ROM or DVD-ROM disc, and disc drive or the like. The memory can be a computer-readable recording medium used to store data in the device 20, and store computer programs or executable instructions that are executed by the device. Moreover, the memory may include smart cards, SIMs or any other medium from which a computing device can read computer programs or executable instructions. As used herein, the term "computer program" is intended to encompass an executable program that exists permanently or temporarily on any computer-readable recordable medium that causes the computer or computer processor to execute the program.

In other aspects the invention includes methods for providing sensory stimulation of a user including introducing and/or presenting, via a weighted lap pad, a multimedia display and/or associated stimulation to a user while engaged with the lap pad 20 described herein.

It should be understood, of course, that the foregoing relates to exemplary embodiments of the invention and that modifications may be made without departing from the spirit and scope of the invention as set forth in the following claims.

What is claimed is:

1. A device, comprising:
   a base having a body-conforming configuration and a plurality of channels having weight material enclosed within each of the channels;
   a first transparent window positioned at a surface of the base and in part defining a first activity device pocket where the first activity device pocket is configured to receive an electronic activity device viewable through the window;
   at least a first hand pocket positioned at a top portion of the base and configured to allow a user to insert a hand into the first hand pocket; and
   a second transparent window is positioned atop the first hand pocket, the second transparent window defining in part a second activity device pocket.

2. The device of claim 1 where a touch-screen enabled activity device inserted into the first activity device pocket may be controlled by touching the first transparent window.

3. The device of claim 1 where the first activity device pocket is configured to receive an activity device having a touch screen display and where the first transparent window is configured such that touching the window allows touch screen control of the activity device having the touch screen display.

4. The device of claim 1 where the plurality of channels span substantially an entire length of the base.

5. The device of claim 1 where the first window spans substantially an entirety of a width of the base.

6. The device of claim 1 where at least one fidget is disposed within the first hand pocket.

7. The device of claim 1 where the first transparent window is configured to receive dry-erase markings such that dry-erase markings may be applied and readily removed from the first transparent window.

8. The device of claim 1 where the device is a lap pad with the base adapted to be placed across a lap of a seated user, the weight material permanently enclosed and sealed within respective channels.

9. The device of claim 8 where the weight material is flowable and has a cumulative weight of between 2 and 15 pounds.

10. The device of claim 1 further comprising a second hand pocket positioned at a top portion of the base and configured to allow a user to insert a hand into the second hand pocket.

11. The device of claim 10 where the first hand pocket and second hand pocket are connected such that a user's hands may touch when inserted therein.

12. The device of claim 1 further comprising an electronic device having a display, the electronic device positioned within the first activity device pocket, the display being touch screen activated by a touch of the first transparent window.

13. The device of claim 1 where the weight material is separately sealed by each of the channels.

14. The device of claim 1 where an open edge of the first activity device pocket is located at a top surface of the base and provides access to the first activity device pocket.

15. The device of claim 1 where the first activity device pocket is stitched along three edges of the first activity device pocket at a top surface of the base with one edge being unstitched to form an opening to access the first activity device pocket.

16. The device of claim 1 where the first transparent window together with a surface beneath the first transparent window at least in part defines the first activity device pocket separated from the weight material.

17. The device of claim 16 where the surface beneath the first transparent window is a top surface of the base.

18. A device, comprising:
- a base having a body-conforming configuration and a plurality of channels having weight material enclosed within each of the channels;
- a first transparent window positioned at a surface of the base and in part defining a first activity device pocket where the first activity device pocket is configured to receive an electronic activity device viewable through the window;
- an electronic device having a display, the electronic device positioned within the first activity device pocket, the display being touch screen activated by a touch of the transparent window, and
- a sensory mechanism positioned on or within the base and responsive to operation of the electronic device.

19. The device of claim 18 where the sensory mechanism includes one from the group of a speaker, heating element, vibrator.

* * * * *